United States Patent
Tesar (10) Patent No.: US 7,918,559 B2
(45) Date of Patent: Apr. 5, 2011

(54) CHOROID AND RETINAL IMAGING AND TREATMENT SYSTEM

(75) Inventor: John C. Tesar, Tucson, AR (US)

(73) Assignee: NOVADAQ Technologies Inc., Mississauga, Ontario (CA)

( * ) Notice: Subject to any disclaimer, the term of this patent is extended or adjusted under 35 U.S.C. 154(b) by 115 days.

(21) Appl. No.: 11/912,944

(22) PCT Filed: May 1, 2006

(86) PCT No.: PCT/US2006/016957
§ 371 (c)(1),
(2), (4) Date: Jul. 29, 2008

(87) PCT Pub. No.: WO2006/119349
PCT Pub. Date: Nov. 9, 2006

(65) Prior Publication Data
US 2008/0291397 A1    Nov. 27, 2008

Related U.S. Application Data

(60) Provisional application No. 60/676,004, filed on Apr. 29, 2005.

(51) Int. Cl.
*A61B 3/10*    (2006.01)
*A61B 3/00*    (2006.01)
(52) U.S. Cl. ........................ 351/221; 351/246
(58) Field of Classification Search .................. 351/221, 351/205, 206, 246
See application file for complete search history.

(56) References Cited

U.S. PATENT DOCUMENTS

| | | |
|---|---|---|
| 2,939,554 A | 6/1960 | Bolton et al. |
| 3,685,221 A | 8/1972 | Mangan |
| 4,102,563 A | 7/1978 | Matsumura et al. |
| 4,149,787 A | 4/1979 | Kobayashi et al. |
| 4,283,124 A | 8/1981 | Matsumura |
| 4,324,083 A | 4/1982 | Johnson, Jr. |
| 4,422,736 A | 12/1983 | Nunokawa |
| 4,572,627 A | 2/1986 | Madate et al. |
| 4,666,268 A | 5/1987 | Ito |
| 4,799,783 A | 1/1989 | Takahashi et al. |
| 5,042,939 A | 8/1991 | Zayek |
| 5,066,116 A | 11/1991 | Sekine |
| 5,214,454 A | 5/1993 | Sano |
| 5,247,318 A | 9/1993 | Suzuki |
| 5,400,791 A | 3/1995 | Schlier et al. |
| 5,444,946 A | 8/1995 | Zeigler |
| 5,483,780 A | 1/1996 | Stumpf |
| 5,557,321 A | 9/1996 | Kohayakawa et al. |
| 5,557,349 A | 9/1996 | Yoneya et al. |
| 5,617,156 A | 4/1997 | Sano et al. |
| 5,729,298 A | 3/1998 | Wester |
| 5,742,374 A | 4/1998 | Nanjo et al. |
| 5,924,258 A | 7/1999 | Castano |

(Continued)

OTHER PUBLICATIONS

Platt et al., "History and Principles of Shack-Hartmann Wavefront Sensing," Journal of Refractive Surgery, 17:S573-S577, (2001).

*Primary Examiner* — Jack Dinh
(74) *Attorney, Agent, or Firm* — Rissman, Hendricks & Oliverio, LLP (57) ABSTRACT

The invention provides an apparatus, a device, and methods for imaging vasculature in a subject as well as an apparatus, a device and methods for treating abnormal vasculature in a subject.

13 Claims, 6 Drawing Sheets

U.S. PATENT DOCUMENTS

| | | |
|---|---|---|
| 6,240,694 B1 | 6/2001 | Castano |
| 6,270,749 B1 | 8/2001 | Blumenkranz et al. |
| 6,350,031 B1 | 2/2002 | Lashkari et al. |
| 6,404,985 B1 | 6/2002 | Ohtsuka |
| 6,456,787 B1 | 9/2002 | Matsumoto et al. |
| 6,546,198 B2 | 4/2003 | Ohtsuka |
| 6,563,626 B1 | 5/2003 | Iwasaki |
| 6,574,432 B2 | 6/2003 | Nanjyo |
| 6,636,696 B2 | 10/2003 | Saito |
| 6,669,339 B2 | 12/2003 | Nanjyo |
| 6,709,108 B2 | 3/2004 | Levine et al. |
| 6,755,526 B2 | 6/2004 | Shibata |
| 6,826,359 B1 | 11/2004 | Takeda |
| 6,968,127 B2 | 11/2005 | Nanjyo |
| 7,052,134 B2 | 5/2006 | Nanjo et al. |
| 7,126,740 B2 | 10/2006 | Szczepanek et al. |
| 2001/0015045 A1 | 8/2001 | Paroly |
| 2002/0152712 A1 | 10/2002 | Smith |

CHOROID AND RETINAL IMAGING AND TREATMENT SYSTEM

CROSS REFERENCE

This application is a National Stage Application from PCT Application Serial No. PCT/US2006/016957, filed May 1, 2006, which also claims the benefit of U.S. Provisional Application No. 60/676,004, which was filed on Apr. 29, 2005 the disclosures of all of which are incorporated herein by reference in their entirety as if fully set forth herein.

TECHNICAL FIELD

The invention relates generally to the field of medical imaging. In certain embodiments the invention provides methods, devices, and an apparatus to visualize, diagnose and treat vascular abnormalities in a subject.

BACKGROUND ART

Vascular abnormalities may occur in a wide variety of anatomical locations and under a wide variety of physiological conditions. As an example, vascular abnormalities occurring in the eye often have significant consequences which may impact the health and well being of a subject. Among the most serious consequences is vision loss.

Vision loss in people over 50 is commonly caused by the localized excessive new growth of blood vessels in the choroid. These concentrations of blood vessels are called Choroidal Neovscular Membranes or "CNVM".

The choroid is the layer of the eye sandwiched between the retina (the light-registering layer) and the sclera (the tough white outer layer that forms the eyeball). The choroid is a vascular layer rich in blood vessels feeding the retina. A very common disease, Age Related Macular Degeneration (ARMD) is associated with the pathologic growth of new blood vessels in the choroid (Choroidal Neovascular Membranes or CNVM) which penetrate the retina and cause vision loss or blindness.

Most retinal imaging devices are designed to visualize, diagnose, or document the posterior anatomy of the eye. The Carl Zeiss Company of Germany has long dominated this field with a series of products that are designed to maximize the field of view, maximize the image quality, and provide recording capability. This was first done utilizing photography and currently is done utilizing electronic cameras. One type of camera is a fundus camera. The fundus camera owes some of its heritage to work done years earlier on the opthalmoscope. The simple design of this device reveals early attempts at visualizing the posterior anatomy of the eye and describes 3 principle methods for introducing light for viewing the back of the eye. The first method involves a beamsplitter that deviates a source of illumination along a path consisting of an optical line of sight between the subject's eye and the observer's eye. The light enters the eye illuminating the eye and the returning light from the retina passes through the beamsplitter and passes to the observer's eye. If the beamsplitter coating is 50/50 then there is an illumination loss both when the beam path is reflected towards the subject's eye and a loss to the returning light that is directed towards the observer. The second example involves deviating the light source off a front surface mirror mounted nominally at 45 degrees where the mirror is comprised of a hole for light to pass from the subject's eye to the position of the observer. This method was later adopted by Zeiss in the design of the fundus camera. The losses in illumination are related to the area ratios between the reflecting surface and the hole. The third method involves the introduction of source illumination to the axis between subject and observer by means of a front surface mirror segment. Similar to the second method, the loss relationships (ratio of reflecting surface area to viewing path) are first established by the cross sectional areas of the total beam diameter. All three of these methods are nominally called beam combining.

Imaging of the posterior segment of the eye, e.g., the choroid, in cases of age-related macular degeneration has evolved rapidly in the past two decades. Infrared light is now routinely used to visualize features not seen by other methods. Typically the light is provided by a laser. With digitization, the ability to acquire, store and retrieve images has greatly improved. Thus it is now possible to diagnose lesions more effectively. Moreover, methods and devices which provide for imaging and diagnosing abnormalities associated with the choroid, as well as for methods of treating those abnormalities have been described (see, e.g., U.S. Pat. Nos. 5,279,298; 5,394,199, both of which are hereby incorporated by reference in their entirety). These devices however are not without their shortcomings. Among these shortcomings was the inability to provide a well corrected virtual image that was free of aberrations and the difficulties associated with repositioning the lasers during either treatment or visualization.

It would be useful to improve upon known methods by providing a method for introducing multiple illumination and treatment sources (lasers) into the eye and multiple imaging paths exiting the subject's eye towards the observer (recording or imaging device, viewing in the visible and or the near IR). The optical devices should be capable of accommodating a large range of optical wavelengths from deep blue to infrared. Additionally, the device should be able to map the curved posterior of the eye to a flat image plane. The device should also be compact and cost effective while producing high quality images having a sufficient field of view. A need therefore exists for improved devices and methods for imaging abnormal vasculature, e.g., vasculature associated with the eye of a subject.

DISCLOSURE OF THE INVENTION

In certain embodiment, the invention provides a device for visualizing one or more of the choroidal neovasculature and the retina. In some embodiments, the device includes a) an afocal assembly comprising an objective assembly and a collimating assembly, wherein the objective assembly is configured to relay a real image of the subject's eye to the collimating assembly, and the collimating assembly collimates the image and relays it to an external pupil in image space; and (b) one or more proximal modules that are in optical communication with the afocal assembly through the external pupil.

In certain embodiments, the invention further provides methods for imaging one or both of a subject's choroidal neovasculature or retina. In some embodiments, the methods include the steps of (a) administering to the subject a dye that emits in the infra red spectrum when it is excited; and (b) imaging the subject's choroidal neovasculature with the device of the invention. In some embodiments, the methods include the steps of administering to the subject a dye that emits in the visible spectrum when it is excited and (b) imaging the subject's retina with a device of the invention.

BRIEF DESCRIPTION OF THE DRAWINGS

The advantages of the invention may be better understood by referring to the following description in conjunction with the accompanying drawings in which.

MODE(S) FOR CARRYING OUT THE INVENTION AND INDUSTRIAL APPLICABILITY

Hereinafter, aspects in accordance with various embodiments of the invention will be described. As used herein, any term in the singular may be interpreted to be in the plural, and alternatively, any term in the plural may be interpreted to be in the singular.

The present invention relates to ophthalmic devices including apparatuses such as fundus cameras, scanning laser opthalmoscopes, retinal imagers, photo-coagulators, etc. Specific embodiments provide optical assemblies and configurations for imaging, recording and treating ocular anatomy in multiple wavelengths with lasers of multiple wavelengths. The apparatus described herein provides several improvements in medical imaging of vasculature, e.g. vasculature associated with the eye. These include the ability to visualize vessels using a plurality of dyes in certain embodiments, and to treat abnormal vessels with the same device, e.g. by photocoagulation in some embodiments. In some embodiments, the devices of the invention can be used to visualize both the retina and the choroidal vasculature. In some embodiments, both can be visualized simultaneously. In other embodiments, the devices of the invention may be configured to visualize just one of the retina and choroidal vasculature.

The apparatus described herein provides radiant energy that is preferably corrected for virtually all aberrations. Thus it may provide a well corrected image, e.g., a Strehl ratio of about 60%, about 70%, about 80% or about 90% The image may be a flat field and thus the radiant energy source in the apparatus is easily focused and positioned. Any wavelength of light may be used as the apparatus provides means of providing well corrected wavelengths of all colors. Thus, in certain embodiments, the apparatus 150 provides a radiant energy source wherein all wavelengths are simultaneously in focus.

DEFINITIONS

Aberration, as used herein, means defects of a lens device that cause its image to deviate from the rules of paraxial imagery.

Absorption, as used herein, means the loss of light as it passes through a material, generally due to its conversion to other energy forms (usually heat).

Achromatic, as used herein, means free of color; a color perceived to have no hue, such as neutral grays.

Afocal as used herein means an optical device with object and image points at infinity.

Aperture as used herein means an opening or hole through which radiation or matter may pass.

Aperture stop as used herein means a physical restraint that limits the diameter of the bundle of light allowed to pass through a lens.

"Approximately", "substantially" and "about" each mean within 15%, preferably within 10%, more preferably within 6%, even more preferably within 4%, and even more preferably within 2%, and most preferably within 0.5%.

Beamsplitter as used herein means an optical device for dividing a beam into two or more separate beams or combining multiple beams into a single beam. Such beamsplitters can be of a dichroic type and are often characterized as short or long pass. A short pass beamsplitter passes a shorter range of wavelengths below its frequency cutoff and reflects wavelengths above its frequency cutoff. The two wavelengths are combined by passing the shorter wavelength through the beamsplitter which is nominally placed at a 45° in the beam path, but can be at some other angle such as, but not limited to 30° or 60°. A second beam path of a longer wavelength is positioned relative to the inclined beamsplitter so that its direction is changed by reflection, where the angle of incidence equals the angle of reflection, and the resulting reflected beams axis is now coincident with the original shorter wavelength beam direction. A long pass filter or beamsplitter reflects the shorter wavelengths and passes radiant energy above the cut off frequency.

Camera as used herein means a light-tight box that receives light from an object or scene and focuses it to from an image on a light sensitive material or a detector.

Chief Ray as used herein means the central ray of any ray bundle. where it—and all other chief rays—cross the optical axis a pupil is defined. When this or any pupil is the limiting aperture of the device then it is considered the stop of the optical device.

Collimation as used herein means the process by which one or more divergent beams of radiation or particles are converted into parallel beams, or a plane parallel wavefront Computer as used herein, refers to a conventional computer as understood by the skilled artisan. For example, a computer generally includes a central processing unit that may be implemented with a conventional microprocessor, a random access memory (RAM) for temporary storage of information, and a read only memory (ROM) for permanent storage of information. A memory controller is provided for controlling RAM. A bus interconnects the components of the computer device. A bus controller is provided for controlling the bus. An interrupt controller is used for receiving and processing various interrupt signals from the device components. Mass storage may be provided by diskette, CD ROM or hard drive. Data and software may be exchanged with computer device via removable media such as the diskette or CD ROM. A CD ROM drive is connected to the bus by the controller. The hard disk is part of a fixed disk drive that is connected to the bus by a controller. User input to the computer may be provided by a number of devices. For example, a keyboard and mouse may be connected to the bus by a controller. An audio transducer that might act as both a microphone and a speaker may be connected to the bus by an audio controller. It will be obvious to those reasonably skilled in the art that other input devices, such as a pen and/or tablet may be connected to the bus and an appropriate controller and software, as required. A visual display can be generated by a video controller that controls a video display. Preferably, the computer further includes a network interface that allows the device to be interconnected to a local area network (LAN) or a wide area network (WAN). Operation of the computer is generally controlled and coordinated by operating device software, such as the Solaris operating device, commercially available from Sun Microdevices, the UNIX® operating device, commercially available from The Open Group, Cambridge, Mass., the OS/2® operating device, commercially available from International Business Machines Corporation, Boca Raton, Fla., or the Windows NT operating device, commercially available from Microsoft Corp., Redmond, Wash. The operating device controls allocation of device resources and performs tasks such as processing scheduling, memory management, networking, and I/O services, among things. In particular, an operating device resident in device memory and running on the CPU coordinates the operation of the other elements of computer. The computer includes software, i.e., program code, on computer readable media.

Distal as used herein refers to the direction toward the objective assembly and away from the proximal module(s) in some embodiments. In certain embodiments it is furthest from the user or physician and closest to the subject when device 150 is in use.

Filter as used herein, means an assembly that attenuates particular wavelengths or frequencies while transmitting others.

Image as used herein, means the reproduction of an object produced by light rays. If a point in object space is transmitted and the beam converges to a point then a real image is formed. If the beam diverges a virtual image is formed.

Lens, as used herein, means a transparent optical component or assembly comprising one or more pieces of optical glass, or other suitable material, with surfaces so curved that they serve to converge or diverge the transmitted rays from an object, thus forming a real or virtual image of that object. A lens may refer to a single transparent optical component or to a plurality of transparent optical components.

Marginal ray as used herein means a ray that passes through an optical device near the edge of the aperture and or lens. A marginal ray bundle contains a central chief ray.

Mixing rod, as used herein, means a glass rod designed such that all light exiting from it is uniformly distributed at a desired numerical aperture.

Numerical aperture as used herein refers to a basic optical characteristic representing the size of an input cone or exiting cone of radiant energy. It is equal to the sine of the half angle of the acceptance cone, or solid angle.

Proximal as used herein means toward the one or more proximal assemblies and away from the objective assembly or subject's eye. In other embodiments, it refers to being closer to the user and further from the subject when the device 150 is in use.

Pupil as used herein, means an opening in the iris that permits light to pass and be focused on the retina forming the limiting aperture or stop of the eye, or the image of the aperture stop as seen from object and image.

Telecentric Lens as used herein refers to a lens designed such that all the chief rays from any ray bundle in either object or image space are parallel. Telecentric lens groups can be designed to be doubly telecentric in both image and object space. Magnification is a product of object distance and the optical power of lenses and lens groupings. A plane moved through best focus of the lens goes into and out of sharp focus, but its image size is constant. If one traces a point in object space through a lens telecentric in image space the ray bundles vary by angle in object space and by a displacement in x or y in image space. Telecentric lenses provide constant magnification for any field point of the object. Telecentric lenses as found in these embodiments have negligible distortion.

Subject as used herein, refers to any animal. The animal may be a mammal. Examples of suitable mammals include, but are not limited to, humans, non-human primates, dogs cats, sheep, cows, pigs, horses, mice, rats, rabbits, and guinea pigs.

Treat, Treatment, or Treating, as used herein each mean any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition; or the prophylaxis of one or more symptoms associated with a disease or condition.

User as used herein refers to a medical professional, e.g., a doctor, optometrist, ophthalmologist, technician, scientist, research, intern, medical resident, or another person who uses the device of the invention to image and/or treat the subject's eye.

Vasculature as used herein refers to the entire circulatory device of a subject.

The Mammalian Eye

Figure 1A:
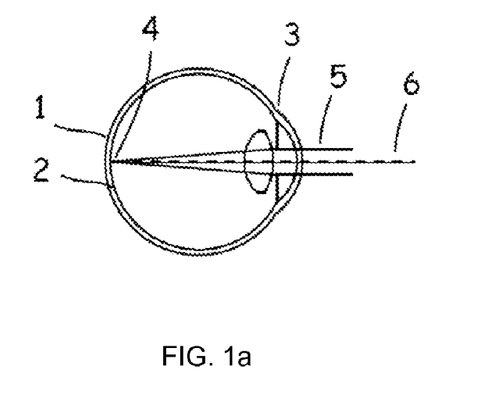
FIGS. 1a and 1b illustrates the human eye with light energy focused on the back of the eye. The radiant energy is focused on the center of the back of the eye in FIG. 1a, and to one edge of the back of the eye in FIG. 1b.
Figure 1B:
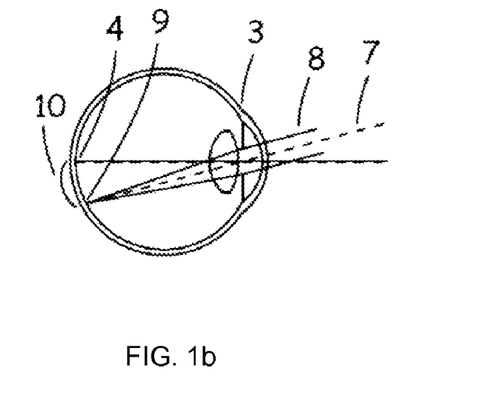

The skilled artisan is well familiar with focusing light energy on a subject's eye. Referring to FIGS. 1a and 1b, ray bundle 5 is directed to the back of the eye. It travels through pupil 3 to the retina 2 and choroid (i.e., choroidal neovasculature) 1. Chief ray 6 is shown. In FIG. 1a, the ray bundle 5 is directed to focal point 4. In FIG. 1b, the ray bundle labeled as 8 (including the chief ray of marginal ray bundle 8) are shown going through pupil 3 to a focal point 9, defining the extreme ray position and perimeter of the field of view of the system. The skilled artisan understand that the pupil 3, which is on the z axis, is the point within the eye where all chief rays pass through the optical axis. Arc 10 illustrates half of the field of view of the choroidal neovasculature, which is distal to the retina and, under ordinary circumstances, is not visible to the user, as the preponderance of equipment used to visualize the retina is not suitable for viewing in the near infra red.

DEVICES OF THE INVENTION

Certain embodiments of the invention provide a device 150 suitable for imaging vasculature in a subject. The device 150 of the invention may also be used to treat abnormality in the choroids or retina present within the vasculature of a subject. Significantly, the device allows imaging of the retina using visible light and/or infrared imaging of the choroidal vasculature.

In one embodiment, the device includes an afocal assembly that receives light from a subject's eye, collimates the light, and transmits it through a pupil that is external to the afocal assembly and further to one or more modules that receive light through the external pupil. The external pupil between the afocal assembly and proximal modules is conjugate to the eye's pupil, making it a virtual pupil.

Figures 2, 2A, 2B, 2C:
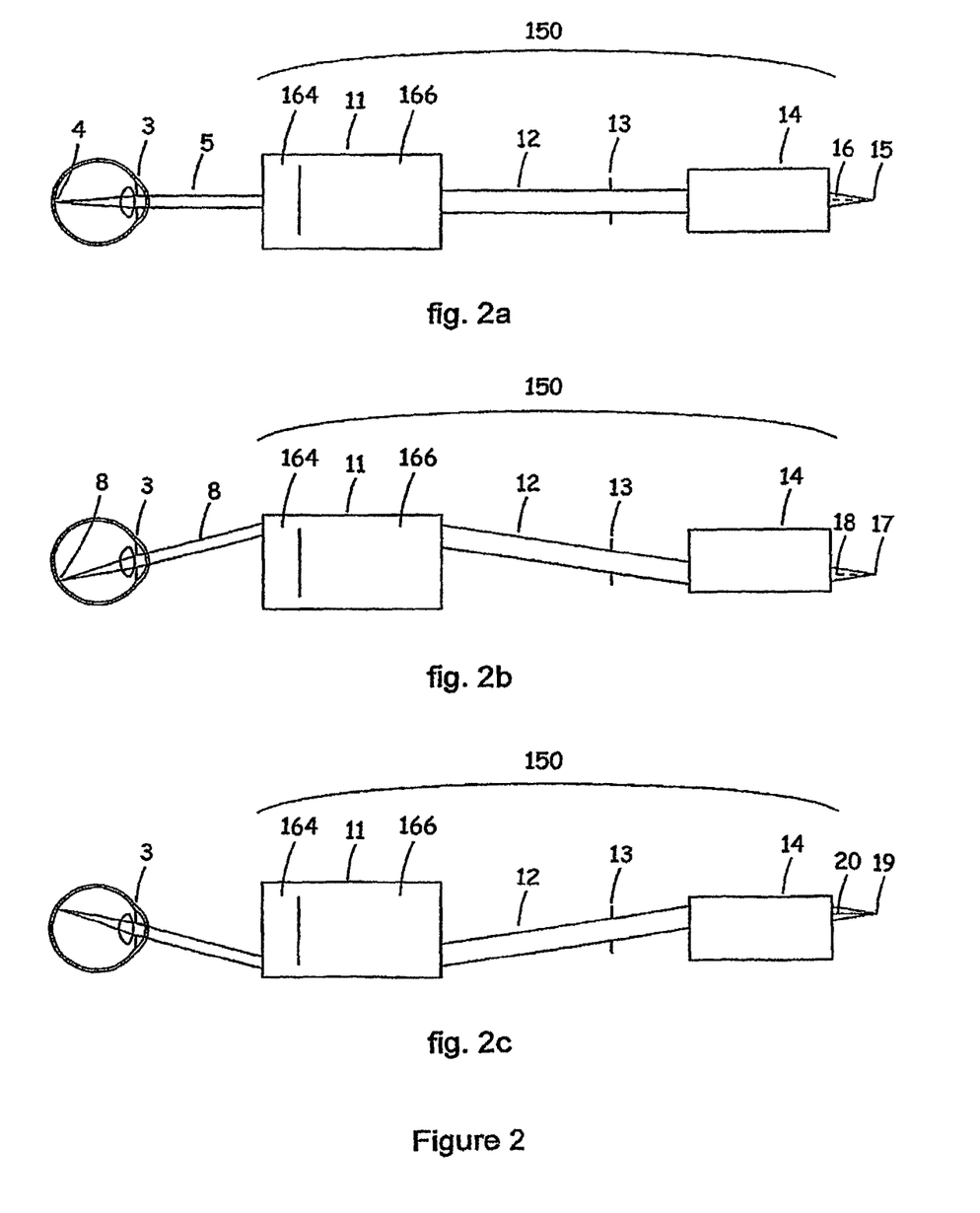
FIGS. 2a-2c illustrate the optical components of a device 150 of the invention as it would interact with a human eye.

The optical elements of device 150 are illustrated in FIGS. 2a-2c as they would interact with a subject's eye (which is not part of device 150). The eye shown in FIGS. 2a-2c is the subject's eye, which is imaged and/or treated with device 150. The eye shown is not physically connected to device 150 but the eye's nominal wavefront errors from a wide field of view are preferably compensated for by device 150.

Referring to FIG. 1a, proximal module(s) 14 transmits light through virtual pupil 13 along path 12 to afocal assembly 11. Afocal assembly 11 transmits the light energy onto the eye as described relating to FIGS. 1a-1b where it is focused on the retina or choroids by the eye's cornea and lens. Light is reflected from the eye back to the afocal assembly 11 which then transmits it along path 12, through a virtual pupil 13 in the collimated space, to one or more proximal module(s) 14. Afocal assembly 11 collimates the light energy and magnifies the ray bundles as shown by the relationship between paths 5, 8, and 12 in FIGS. 2a-2c, permitting a larger virtual pupil of the eye's pupil facilitating division by multiple proximal modules 14.

Preferably, multiple proximal modules receive light energy from virtual pupil 13 or relay light energy through virtual pupil 13 to afocal assembly 11. At least one of these proximal modules is an illumination module which is used to excite one or more dyes in a subject's eye. The device 150 further preferably includes at least one imaging module for detecting light emitted by the excited fluorescent dye(s) and thus forming an image of the eye. Yet other proximal modules that can be used within the scope of the invention are described below.

Each of these components, including elements 15-20 will be described in more detail below.

Afocal Assembly 11

The afocal assembly 11 receives light from the eye of the subject (see, e.g., FIGS. 2a-2c) and focuses it into a virtual pupil 13 in image space, i.e., outside the afocal assembly 11 and proximal module(s) 14. The virtual pupil 13 is the point along the z axis where the chief rays from all field points on the retina 2 cross the optical axis. The virtual pupil is conjugate with the subject's eye's pupil. The virtual pupil 13 is also the conjugate image of the eye's pupil 3. The virtual pupil 13 is preferably larger than the eye's pupil 3 in at least one dimension, and preferably in two dimensions. Thus the afocal assembly 11 preferably magnifies as well as reimages the eye's pupil 3.

In certain embodiments, afocal assembly 11 includes an objective lens assembly 164, containing an optional deviating prism or mirror assembly. Afocal assembly 11 further includes collimating lenses in section 166. The combination of lenses in the objective and collimating assemblies are designed to collimate and preferably magnify the light exiting the eye to produce an external pupil 13 in collimated space; and preferably, by the addition of compensating errors offset the nominal errors of the human eye. This is accomplished by the selection and use of glass types, measured by their index of refraction, their abbe number (the measure of their dispersion) and their partial dispersion. These three measures are known to those skilled in the art of optical design. Additionally, the design preferably incorporates the ability to move the collimating lens or lens group along the z axis to compensate for the variation in refractive error of the subject's eye. Table 1 shows an exemplary prescription for an objective lens group making up an objective lens assembly 164.

TABLE 1

| Objective Lens Group | | | | |
|---|---|---|---|---|
| S | Radius | Thickness | Index | Dispersion |
| 1 | 244.06 | 14 | 1.487 | 84.468 |
| 2 | −38.961 | 1 | | |
| 3 | 80.584 | 18 | 1.487 | 84.468 |
| 4 | −33.738 | 5 | 1.750 | 34.820 |
| 5 | −105.93 | | | |

The objective lens or objective lens assembly creates an aerial image of one or more of the retina and the choroid that is received from the subject's eye. It further relays the real image to a collimating lens or lens group inside afocal assembly 11.

Afocal assembly 11 thus collimates the light received from objective 164 in space 166 inside afocal assembly 12. Collimation can be achieved by a group of 2 or more positive powered lens or group of lenses (hereinafter plus lens) and a minus lens or lens group that together form a Galilean afocal telescope, with the first distal lens or group of lens having positive power, in either case.

In certain embodiments, the afocal assembly 11, includes two positive groups that include a focal point and on each side have collimated space. In other words each lens group is used at its nominal focal length positioned to form a real image of the retina/choroid within the assembly 11 between sections 164 and sections 166.

Table 2 illustrates a prescription for a set of lenses used to collimate light in section 166 of afocal assembly 11.

TABLE 2

| Collimating Optics Group | | | | |
|---|---|---|---|---|
| S | Radius | Thickness | Index | Dispersion |
| 1 | 122.32 | 5.42 | 1.603 | 38.030 |
| 2 | 42.781 | 8.50 | 1.487 | 70.406 |
| 3 | −30.287 | 17.00 | 1.713 | 53.832 |
| 4 | −61.748 | 5.00 | | |

Afocal assembly 11 further includes an external pupil 13 on its proximal side through which light energy is relayed to proximal modules 14 and received from proximal modules 14. Preferably, the afocal assembly 11 magnifies the diameter of the ray bundle received from the eye that it transmits through the external pupil 13 towards the proximal modules 14. In other words, there is preferably a greater ratio than 1:1 between the ray bundle diameter received from the subject's eye and the ray bundle diameter relayed to proximal modules 14 via external pupil 13. Preferable, the afocal assembly 11 is well corrected for all wavelengths between blue and near infrared, with a Strehl ratio of about 60%, about 70%, about 80% or about 90% in at least one, preferably a plurality, and more preferably a majority and most preferably approximately all wavelengths relayed by the afocal assembly 11 to proximal modules through virtual pupil 13. Additionally, the majority and preferably all continuous ray bundles that pass from the afocal 11 through the external pupil, 13, to the proximal modules 14 define the field of view at the back of the eye and map to the displacement in telecentric space of the proximal module for the motion range in x and y of fiber sources for illumination, treatment or patient eye fixation. For imaging modules this angular range of the bundles going through the external pupil define the field of view of the detector. A detector size can be chosen in advance and the focal length chosen to produce the necessary field of view to cover the detector or desired portion of the detector. The imaging module requires an external entrance pupil matched, in angle space, to that of the afocal module. A portion of the pupil 13, is used.

Use of a flat field low distortion telecentric module, as revealed in the proximal ITF module, within the device 150 means that the z dimension does not need to be considered when aiming light or other energy to or away from the eye. This is particularly useful since the posterior of the eye is curved, but with such a module 14; a flat rendition of the retina or choroid is produced. For example, referring again to FIGS. 2a-2c, fiber tip 15, is shown along with its chief ray 16. Fiber tips 15, 17, and 19 are connected to optical fibers that transmit light from an energy source, e.g., a laser, to modules 14, which then transmit the radiant energy to virtual pupil 13.

Collimation is made possible by a well-corrected afocal assembly 11. In certain embodiments, the afocal assembly 11 provides a mechanism for correction for one or more of the errors that may be unique to a subject, i.e., hyperopia, myopia and/or astigmatism. Such correction can be done by one or both of changing the relative location of the lens group that collimates light. (i.e., plus/minus, plus/plus or plus/plus/plus), or by introducing a lens or lens group to correct errors that are unique to the subject.

These aberrations may be corrected in several ways. In certain embodiment, the user can change the distance along the optical axis inside the afocal assembly 11. For example, the device of the invention 150 may have a focusing knob that cooperates with the lenses in the afocal assembly 11. A user can thus adjust one or more of the focusing knobs to move the positions of the lenses along the optical axis and hence correct for subject-unique aberrations.

In certain embodiments, a subject's unique eye aberrations may be corrected by the user's insertion of one or more lenses or pairs of crossed cylinders into afocal assembly 11 along the optical axis 152. For example, the afocal assembly 11 may have slits that are configured to receive optical elements, such as crossed cylinders as described in U.S. Pat. No. 4,732,466, which is hereby incorporated by reference in its entirety. Others such devices are described in other U.S. patents having Inventor: Humphrey; William E. (San Leandro, Calif.) and assigned to Humphrey Instruments, Inc.

In certain embodiments, a subject's unique eye aberrations may be corrected by the user's insertion of one or more lenses or pairs of crossed cylinders into afocal assembly 11 along the optical axis. For example, the afocal assembly 11 may have slits that are configured to receive optical elements, such as crossed cylinders as described in U.S. Pat. No. 4,732,466, which is hereby incorporated by reference in its entirety.

Virtual Pupil 13

The virtual pupil 13 is preferably larger than the size of the subject's pupil.

FIG. 3 illustrates multiple exemplary embodiments of a virtual pupil 13. Arrows originating outside the virtual pupil represent light traveling in a different direction than arrows originating within the virtual pupil.

Since the human pupil 3 is approximately circular, the virtual pupil 13 will also be approximately circular as well.

Figure 3A:
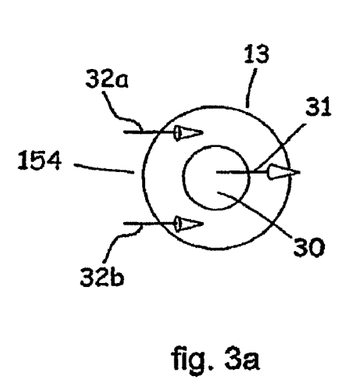
FIGS. 3a-3f illustrate multiple examples of virtual pupils.
Figure 3B:
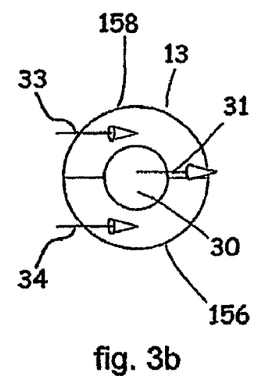
Figure 3C:
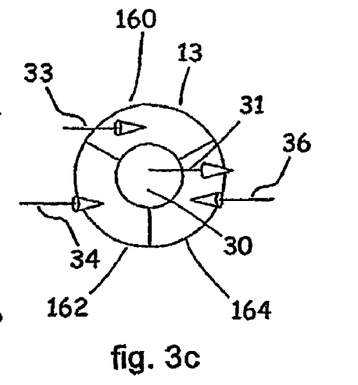

Referring to FIGS. 3a-3c. the virtual pupil 13 will have at least one approximately circular portion, e.g. section 31, within virtual pupil 13, in the approximate center of virtual pupil 13. Section 31 can have a diameter of 3.75 mm, for example, or between about 3.5 mm and about 4 mm, and other diameters are within the scope of the invention Afocal assembly 11 and proximal modules 14 will be preferably configured so that the space inside section 31 is substantially allocated to light returning from the eye to the proximal modules 14 (e.g., indicated by arrows 31). It is advantageous to use the central portion of the cornea for returning radiant energy for one or more imaging modules as the central portion of the cornea will reflect energy back into the device if it is used for that purpose. As further described below, one of the proximal modules 14 is an imaging module that includes detectors for detecting light received from the eye.

As shown in FIGS. 3a-3c, the remainder of the virtual pupil 13 space is used for radiant energy traveling from one or more proximal modules 14 to afocal assembly 11. In FIG. 3a, space 154 is allocated for light transmitted from one or more proximal assemblies 14 to the afocal assembly 11, as indicated by arrows 32a and 32b. Light energy 32a and 32b may be from the same proximal module 14 or from multiple proximal modules. They may be at the same or different wavelengths.

Referring now to FIG. 3b, it is often useful to separate light energy from different proximal modules 14. For example, a device 150 may include a first proximal module 14 for irradiating dye that emits light at a first wavelength (i.e., an illuminating module), and a second proximal module 14 for photocoagulating a dye at a second wavelength. The first and second wavelengths may be different. In such embodiments, light energy of the first wavelength (illustrated by arrow 33) may be transmitted through zone 158, while light energy of the second wavelength (illustrated by arrow 34) may be transmitted through zone 156. Again referring to FIG. 3b, in one embodiment, zone 33 may be allocated for light from one or more illumination sources, preferably together emitting both visible and near IR radiation. Such radiation may be delivered to a mixing rod (shown in FIG. 4) by fiber optics and re-imaged onto the upper portion of the beam combining prism 17 (shown in FIGS. 5 and 6). The numerical aperture of the fiber optics can be modified in the mixing rod or by the use of optics. In a Koehler arrangement light is focused on the pupil position forming an image at the virtual pupil as opposed to passing collimated light through the pupil towards the afocal assembly, commonly called critical illumination.

Figure 4:
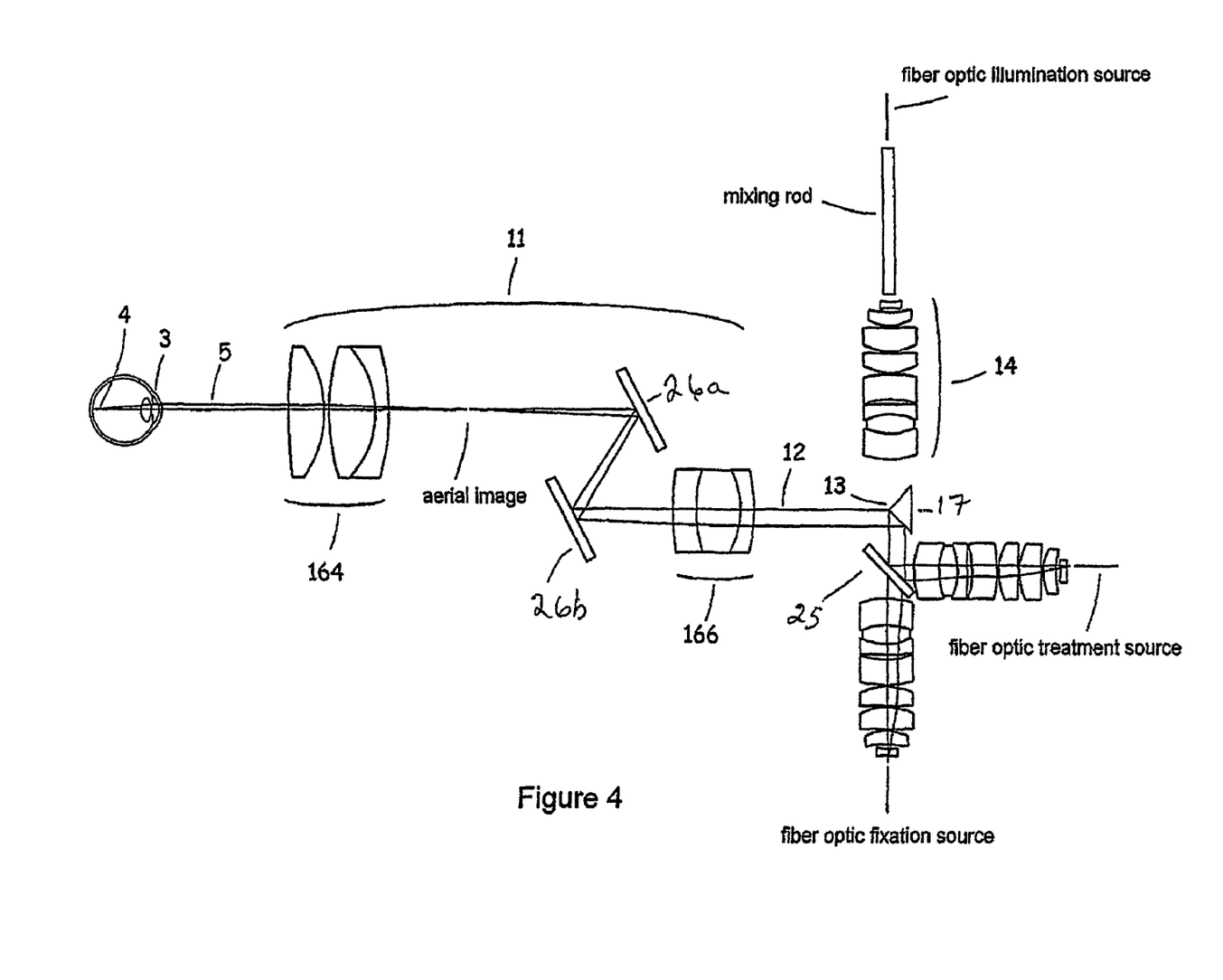
FIGS. 4, 5, and 6 illustrate embodiments of device 150.
Figure 5:
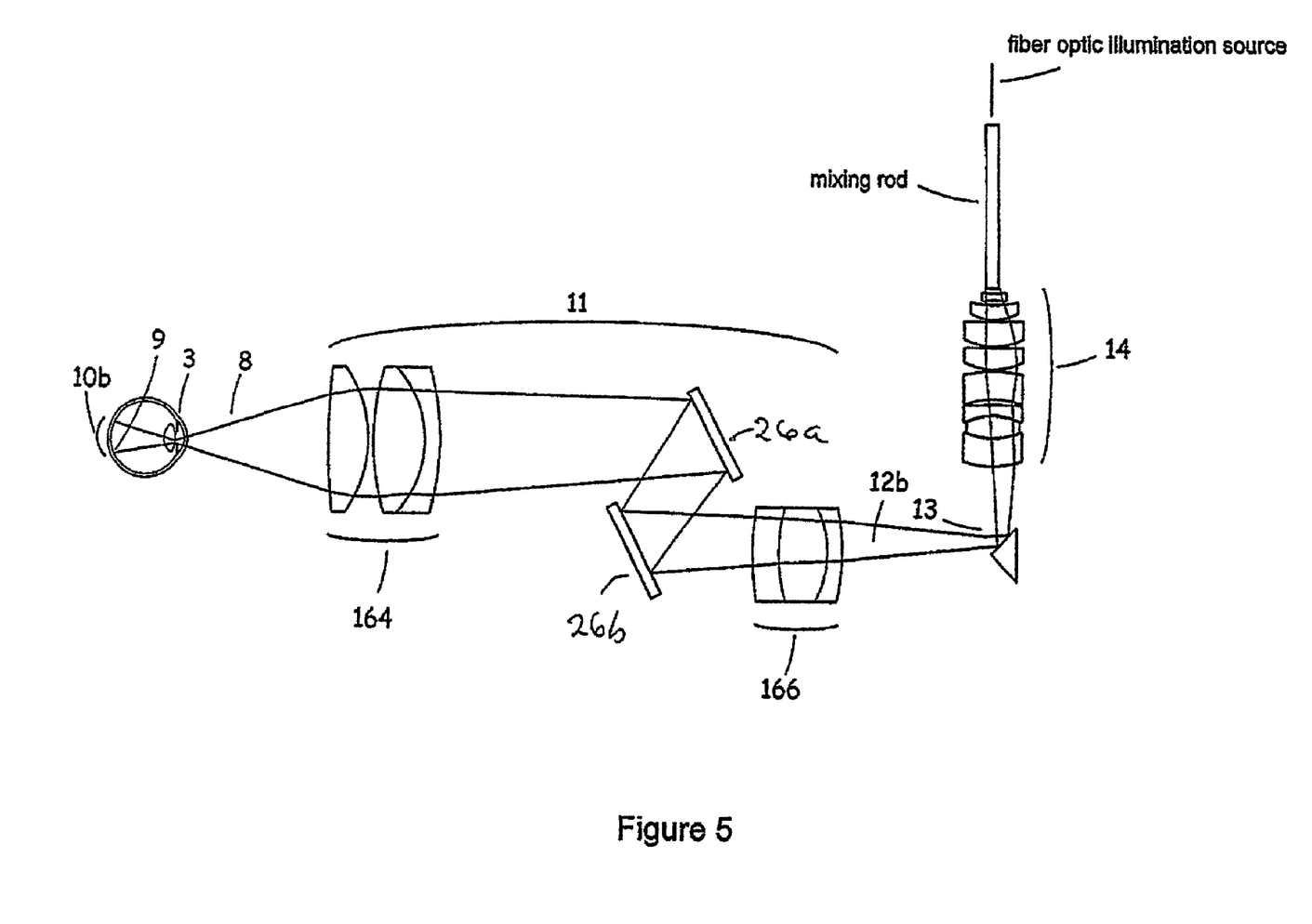
Figure 6:
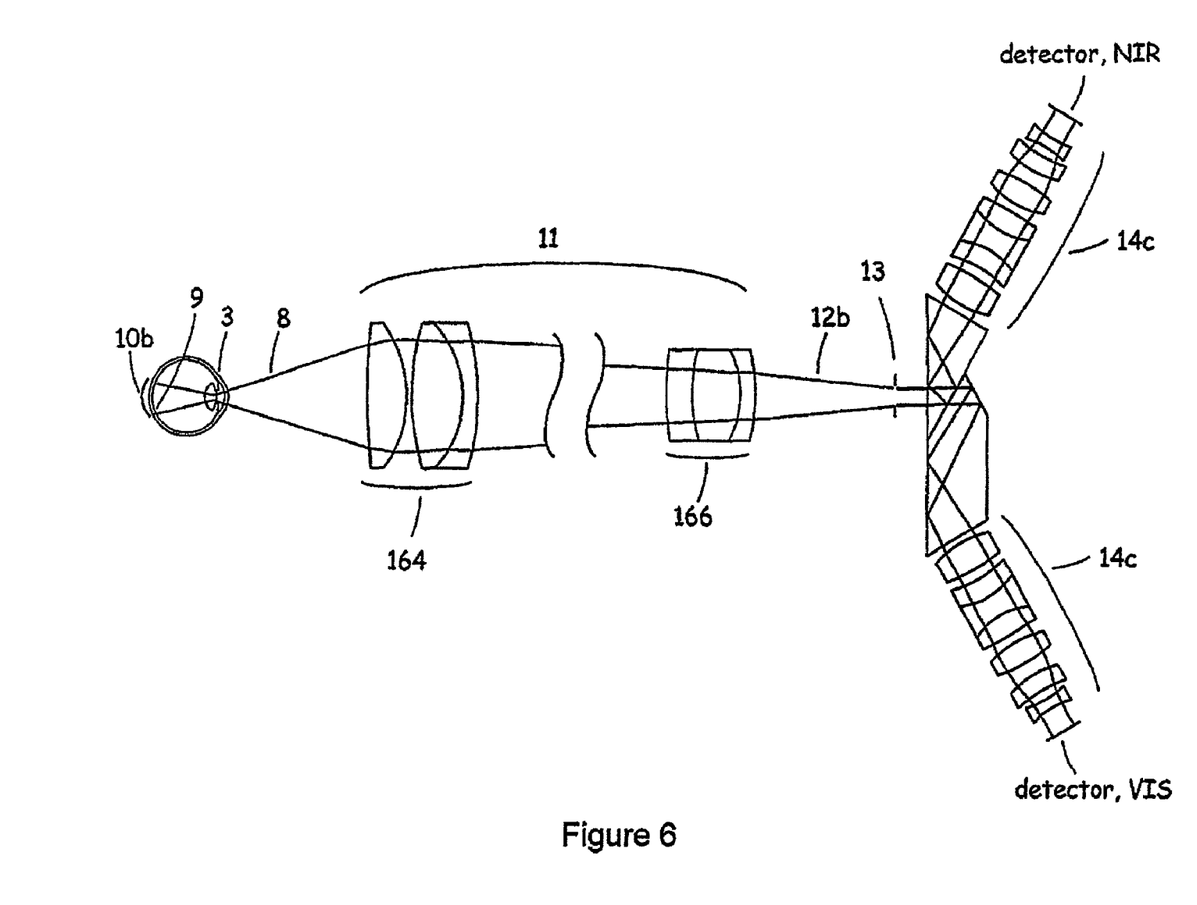

Referring now to FIGS. 4, 5, and 6, in certain embodiments, zone 34 is further allocated for multiple wavelengths entering the virtual pupil 13 from multiple proximal modules, the treatment proximal module and the fixation module, by means of a short or long pass dichroic beam-splitter 25 (shown in FIG. 4). For example, the NIR laser source emitted by a fiber at the focal position of the imaging proximal module is reflected off the surface of a short pass beam-splitter and a low power aiming laser, characterized by a shorter wavelength such as 632 or 635, or 675 nm, or another wavelength) is transmitted by a fixation proximal module used at its focal point position on the z position of the fiber optic tip through the beam-splitter and directed towards the lower portion of the virtual pupil, e.g., zone, 34.

In some embodiments, a metallic beam-splitter 25 is used. In some embodiments, the ratios of transmission and reflection are equal, e.g., 50/50 between different wavelengths. In some embodiments, the ratio may be about 90/10, about 80/20 or other favorable ratio where the larger flux path is reserved for the treatment proximal module beam, as it is certain to be advantageous to reserve more power for the treatment wavelength path than that the fixation source.

As a further example, FIG. 3c shows the space outside the inner circle 30 divided into three segments 160, 162 and 164. Light 33, 34, and 36 may original from one, two, three, four, or more proximal modules and may be at any number of wavelengths.

Figure 3D:
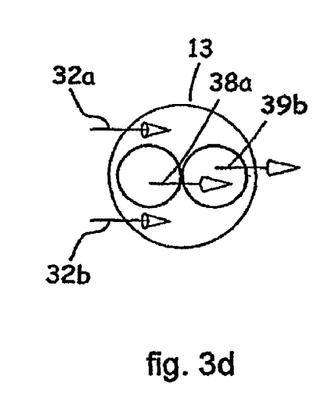
Figure 3E:
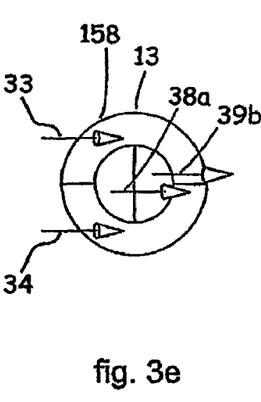
Figure 3F:
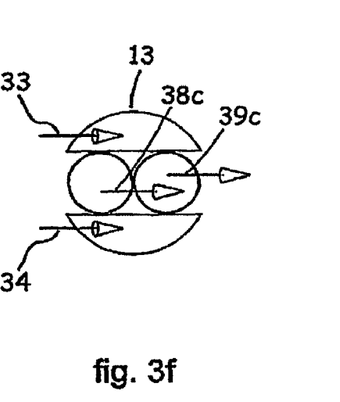

Referring now to FIGS. 3d-3f, space 30 may be subdivided into two or more areas as shown. Each of the two subdivisions may be used to relay light to a different imaging proximal module. Hence, the user (e.g., a doctor), would see the subject's eye stereoscopically (i.e., a first image of light received from space 38 and a second image of light received from space 39). In some embodiments, each of the halves of section 31 may be used to transmit infrared light. In certain embodiments, each may relay only visible light. In yet other embodiments, one may transmit energy in the visible spectrum and yet another may transmit energy in the infrared spectrum.

For example, the eye may reflect visible light and may also include an excited fluorescent dye that simultaneously emits radiation in the infrared spectrum. Thus, in certain embodiments, both the visible and infrared wavelengths may be transmitted through space 30 (FIGS. 3a-3c). In certain other embodiments, space 30 may be split into multiple separate zones, such as spaces 38a and 39a as shown in FIG. 3d, spaces 38b and 39b as shown in FIG. 3e, or spaces 38c and 39c as shown in FIG. 3f. In yet other embodiments, space 30 may be divided into more than two zones.

The skilled artisan will understand that a virtual pupil 13 is in collimated space. Thus, a first portion of space might be separated from a second portion of space in the sense that different light energy of different wavelengths is directed through the first or second portion, or in that the energy is directed through the first and second space in different directions, in different frequency space, and in different time domains.

Thus, as described, wavelengths of different energy and of different directions are transmitted through different sections or zones of virtual pupil 13. Light is relayed through different segments by use of beamsplitters present within afocal assembly 11 (for light traveling from the eye to one or more proximal modules) and other optical elements that are well known to the skilled artisan. Such beamsplitters are preferably closer to the proximal end of the afocal assembly 11 (i.e., closer to the end of assembly 11 that is closest to the proximal assemblies 14 than the end of assembly 11 that is closest to the eye when device 150 is in used to image a subject's eye).

For example, a beamsplitter prism may be used to separate infra red light from visible light in the imaging path. There may be multiple reflections in the beamsplitting assembly and they may have a first gold or silver coated surface for reflecting infrared wavelengths (and transmitting light in the visible spectrum) and a second glass surface for reflecting light in the visible wavelengths in addition to one or more beamsplitters which direct certain wavelengths to certain detectors. Gold coatings are preferably applied directly to the reflecting prism surface and are between 1 and 20 micrometers in thickness, and preferably between 1 and 10 micrometers in thickness. They can be purchased from, for example, TYDEX J.S. Co. (St. Petersburg, Russia) and vapor deposited onto the surface of interest by any number of thin film coaters in the world using vacuum deposition chambers. Gold coatings are especially preferred because they are known to reflect well in the near IR and withstand autoclaving processes.

Light energy from proximal module(s) 14 to afocal assembly 11 may be directed through virtual pupil 13 through the use of combining prism assemblies, mirrors and other optical elements well-known to the skilled artisan.

FIGS. 4, 5, and 6 multiple embodiments of device 150 Starting at the object side, this optical system 150 includes an objective lens assembly 164 (including a first lens of positive refractive power and a second lens group of positive refractive power, optical distance, a folding and path shortening prism assembly or mirrors 26 (e.g., mirrors 26a and 26b), a lens assembly 166 with a plurality of lenses for collimating the aerial image. Combining prism assembly 17 acts as a switchboard for the device, combining beam paths coming and going.

The most distal lens group is an objective lens assembly 164, a first lens of positive refractive power, a second lens group of positive refractive power, comprising a positive and negative lens. This, or another plurality of lenses of more or less elements and potentially including aspheric elements, may be designed to form an aerial image within the device 150 that will be reimaged by the collimating lens group 166. The objective lens group can be 'focused' or repositioned to cancel refractive error, when present, in the subject's eye. Alternatively, the objective lens assembly 164 can be held stationery and the other elements moved collectively.

The optical space may be varied to change the focus of the device in the event of refractive error in the subject eye.

The folding prism (mirror) assembly 26 (e.g., 26a and 26b) is comprised of one or more prisms (mirrors) used to shorten or reposition the optical axis to make the overall size of the optics head smaller.

The distal collimating lens 166 is a plurality of lenses used to collimate the combined optical system of the emmetropic subject eye, a nominal optical space, the objective lens assembly, the folding mirror or prism assembly, and the distal collimating lens assembly itself. The collimated beam path emanating from the collimating lens assembly 166, must be a well corrected beam, as defined above, whose diameter and angular direction, corresponding to any field point on the back of the eye (within the field of view), predisposes the beam to fully intercept and be coincident with the entrance pupil of the multiple proximal collimating lens assemblies on the other side of the beam distal combining prism assembly.

The beam combining prism assembly 17 is coincident with the entrance pupils of the collimating lens assemblies on either side of it. This beam combining prism assembly may act as a switchboard for the device, combining beam paths coming and going. There are two classes of paths managed by the beam combining prism assembly. A transmitting path beam directed to the subject's eye, and a receiving path beam that is directed to the imaging system. Two transmitting paths may be reflected off the front surface mirror faces of a chisel prism (a beam combining prism assembly) and directed toward the subject's eye. One of the transmitting paths contains illumination of wavelengths of light from blue to the near IR. This energy is combined from fiber optic sources in a mixing rod of sufficient length and of sufficient diameter to fill the 'image' plane of the proximal collimating lens assembly with uniform illumination of a numerical aperture matching that of the fiber sources and of the proximal collimating optics. The other transmitting path is nominally 180 degrees from the first path and aimed at the opposing front surface mirror face of the chisel prism and also directed toward the subject's eye.

The second transmitting path can itself be made up of two or more transmitting paths combined with a combining prism or other beam combining device. For example, one path can be the output of a proximal collimating lens group whose source is a near IR, e.g., 800 nm, solid state laser fiber face, whose position may be moved by the observer within an x and y image plane of the proximal collimating lens group. The movement may be achieved by a joystick combining electro-mechanical and computer controllable and recordable actions, or other means. The x and y motion in this image plane or either transmitted path may be mapped to the curved back of the subject's eye. There is no curved image space at the fiber source position thus making the laser positioning on the back of the eye more controllable and repeatable.

The two faces of the chisel prism contain a hole for the receiving optical path of the system that also serves as the stop of the system with the addition of an optional aperture plate bonded between the chisel prism and the beamsplitter assembly that follows.

The beamsplitter assembly in the imaging or receiving path allows the beam to be divided into two or more paths and directed by folding prisms, mirrors, or right angle prisms towards receiving cameras in the imaging proximal modules described below. The cameras or detectors can be black and white or color cameras and filters can be inserted between the beamsplitter and the final image path to confine each camera to a spectral band, visible for example from blue to red, or near IR.

The cameras can be used simultaneously or separately with images overlaid on a monitor, or separately to two monitors, or to 'digital' binoculars (where 2 separate views, visible or near IR, can be seen by each eye, or the same multiple overlaid image, both visible and near IR, seen by each eye.)

The two image paths, visible for the retina and near IR for the choroid when ICG dye is used, can be indexed to each other for reference and studied. Images from the choroid and its physiology can be shown relative to their position to the retina.

Proximal Modules 14

As described above and shown in FIG. 8, one or more proximal modules 14 may be included in device 150. Proximal modules can be used to illuminate, image, record images, fixate the eye, or perform other functions. Preferably, each of these modules receives and transmits light energy through a different section or zone of virtual pupil 13.

One or more proximal modules 14 may be sold installed on a device of the invention 150, e.g., a fundus camera. In certain embodiments, one or more modules 14 can be installed on the device by the user, e.g., a ophthalmologist or a technician, using a common mechanical interface such as grooves on the module that are sized to mate with receiving ridges on the device 150.

Modules 14 that may be used within the device of the invention 150 must have an external entrance pupil that does not exceed the size or diameter of the virtual pupil 13. The external entrance pupil is on the outside of the proximal module 14 but is generally inside device 150. The external entrance pupil is aligned to receive light energy from at least one section or zone of virtual pupil 13 and/or to transmit light energy through at least one section or zone of virtual pupil 13.

Suitable treatment and fixation modules must only use telecentric optical components (e.g., lenses, surfaces, etc.) to relay treatment and fixation beams (i.e., energy) and to also collimate light energy. Table 3, below, provides an example of a prescription for telecentric and collimating lenses that may be used. Table 3a provides a prescription for an imaging module, and Table 3b provides a prescription that can be used in an illumination, treatment or fixation module.

TABLE 3

Table 3a: Imaging Module

| S | Radius | Thickness | Index | Dispersion |
|---|--------|-----------|-------|------------|
| 1 | 30.726 | 9.70 | 1.487 | 84.468 |
| 2 | −76.076 | 3.39 | | |
| 3 | −36.517 | 6.50 | 1.620 | 36.366 |
| 4 | −23.207 | 7.00 | 1.609 | 46.442 |
| 5 | 23.207 | 7.20 | 1.487 | 84.468 |
| 6 | −183.02 | 2.87 | | |
| 7 | 25.119 | 7.60 | 1.487 | 84.468 |
| 8 | −48.348 | 4.49 | | |
| 9 | 20.388 | 6.50 | 1.487 | 84.468 |
| 10 | 325.46 | 2.65 | | |
| 11 | −21.909 | 3.00 | 1.713 | 53.832 |
| 12 | 21.909 | 4.32 | | |
| 13 | Infinity | 2.00 | 1.522 | 59.483 |
| 14 | Infinity | 2.00 | | |

Table 3b: Illumination/Treatment/and/or Fixation Module

| S | Radius | Thickness | Index | Dispersion |
|---|--------|-----------|-------|------------|
| 1 | 29.640 | 9.50 | 1.805 | 25.432 |
| 2 | 26.227 | 7.00 | 1.487 | 84.468 |
| 3 | −18.701 | 3.50 | 1.613 | 44.295 |
| 4 | Infinity | 2.06 | | |
| 5 | −28.387 | 3.50 | 1.581 | 40.851 |
| 6 | Infinity | 5.75 | 1.487 | 84.468 |
| 7 | −43.714 | 0.50 | | |
| 8 | 19.810 | 7.40 | 1.487 | 84.468 |
| 9 | Infinity | 0.50 | | |
| 10 | 22.387 | 8.40 | 1.487 | 84.468 |
| 11 | Infinity | 0.50 | | |
| 12 | 16.079 | 5.10 | 1.487 | 84.468 |
| 13 | 62.643 | 1.46 | | |
| 14 | −15.963 | 2.50 | 1.581 | 40.851 |
| 15 | 15.963 | 2.50 | | |

In some embodiments, the imaging module(s) have an entrance pupil that is distal to the telecentric lens assembly (e.g., an assembly such as that described in Table 3a). Distal means that the entrance pupil is between the afocal assembly 11 and the first surface of the lens assembly of the imaging module that is closest to the afocal assembly. In some embodiments, the entrance pupil of the imaging module is distal to the telecentric assembly and at the approximate focal distance of the telecentric lens assembly. For example, in one embodiment, the telecentric lens assembly of the imaging module has a focal length of 41.6 mm and an external entrance pupil that is 39.5 mm distal to the first surface of the lens assembly.

The skilled artisan will understand that any illumination, fixation and treatment modules that are part of device 150 transmit light to afocal assembly 11. Thus, these modules might receive light energy, e.g., through a fiber optic that is associated with a light source.

Each of the proximal modules for illumination, treatment and fixation has an entrance pupil that is external to the lens groupings of each module. For example, in some embodiments, where the illumination input fiber numerical aperture is approximately 0.22 in an illumination, treatment or fixation module, it has a telecentric lens assembly having a focal length of approximately 26.5 mm and the entrance pupil of the module is approximately 32 mm distal to the most distal surface of the telecentric lens assembly.

Thus, proximal assemblies for treatment, imaging and fixation collimate beams of light energy traveling from the proximal assemblies 14 to afocal assembly 11. Similarly, as described above, afocal assembly 12 collimates light energy that is relayed to virtual pupil 13 (and hence to proximal assemblies 14). Thus, all chief rays are parallel in image space, defined as the space between the last surface above (15) and the fiber tip. This image plane is a flat field and is conjugate with the back of the eye. The retina and or choroid is represented by a flat field. This means that the radiant energy used for treatment and fixation does not need to take the z axis motion into account, but rather only translation in x and y to reimage a laser spot, for treatment or fixation, on any point of the retina or choroid.

Fixation Proximal Module

In one embodiment, the device includes or is adapted to receive a fixation proximal module. The module is used for providing a point in space at which the patient should look since the direction of the subject's gaze determines the position of the fovea.

The module includes or is in optical communication with a light source, e.g., a laser diode, that emits light energy in the visible spectrum. For example, the light energy might be red, such as 632 or 635, or 675 nm respectively. Suitable sources include lasers and laser diodes which may be optically connected to a fiber optic that is part of fixation module. The proximal collimating lens group is optically corrected to transmit the wavelengths transmitted, and preferably any visible or NIR wavelength.

Preferably, the fixation module, contains an aiming beam of light that is delivered to the back of the subject eye, coincident with the fovea. When the fiber is translated the patient's eye tracks the motion of the spot and directs his or her gaze in a direction that allows the user to direct the treatment beam towards the area of treatment interest and away from the fovea. The fixation beam can be flashed or modulated to hold the subject's attention so that he/she does not follow the coincident aiming beam of the treatment laser used by the user to aim the radiant treatment energy.

Illumination Proximal Module

As described herein, a fluorescent dye is administered to the subject. In one embodiment, the fluorescent dye is excited and emits in the infrared spectrum.

The first step in imaging a dye (that is administered to a patient) that emits in the infrared spectrum is to excite the dye. Energy must be applied in a sufficient amount to cause the dye to fluoresce. Preferably, the energy is light energy. The dye may be excited in the visible, ultraviolet or infrared spectrum. Preferably, the dye is a fluorescent dye, and even more preferably a tricarbocyanine dye, such as indocyanine green. Indocyanine green (ICG) may be purchased from Akorn, Inc., Buffalo Grove, Ill. Use of ICG is described in, for example, U.S. Pat. Nos. 5,394,199 and 5,279,298. Once excited, ICG emits in the infra red spectrum at about 825 to about 835 nm.

In certain embodiments, the imaging proximal module only receives light in the infrared spectrum. In other embodiments, it receives radiant energy in both the infrared and visible spectrums.

In some embodiments, the illumination proximal module includes one or more light emitting diodes (LEDs) that emit light in the infrared spectrum. Light sources may be bulbs or arc sources of metal halides, halogens and xenon that emit in the infra red wavelengths.

In certain embodiments, high power laser diodes (HPLDs) may be used within the scope of the invention. Examples of HPLDs include AlInGaAsP lasers and GaAs lasers which are well known in the art. Such sources can be single diodes (single emitters), or diode-laser bars, which are made from edge emitting semiconductor chips. Such sources can be operated in continuous mode (CW), quasi-CW, or pulsed mode. HPLDs would transmit light through a fiber optic, having a fiber point (e.g., point 15 in FIG. 2a).

The excitation wavelength, $\lambda_e$, of ICG is 805 nm in whole blood. The range of excitation wavelengths capable of exciting ICG ranges from approximately 710 nanometers to 840 nanometers, or more. This range overlaps the fluorescence range of ICG whose peak, $\lambda_f$, is 835 nanometers. It is therefore necessary to use a narrow source such as an HPLD or similarly filtered Xenon source of radiation by means of an excitation or primary filter.

HPLDs, made of AlInGaAsP/GaAs, have as their peak nominal output a wavelength of 808 nm, with a tolerance of +/−3 nanometers. A driving circuit is necessary to provide power to the HPLD, the current and voltage of which can be varied to lower the peak wavelength to 805 nm, the peak absorption of ICG. In other embodiments, where a different dye is used, the peak wavelength will be adjusted to the absorption of that dye.

The laser may optionally include a filter, e.g. a bandpass filter, to ensure that the emitted radiation is of a substantially uniform wavelength. The laser may comprise optics for diverging the laser. The optics may be adjustable permitting variation in the field of illumination. The adjustable optics may also be used to provide even illumination over a given area. In some embodiments the laser output lasts for about 30 seconds. In other embodiments the laser output lasts about 0.5 seconds-about 60 seconds.

In some embodiments the source of the light energy is an incandescent light with an appropriate filter so as to provide a suitable wavelength of light to induce the fluorescent dye to fluoresce.

Visible Illumination Module

In some embodiments, the device includes or is configured to receive a visible illumination module. The module receives light in the visible spectrum through the virtual pupil 13 to afocal assembly 11. It includes one or more of the following light sources or is in optical communication with one of them: White light LEDs, bulbs or arc sources of metal halides, halogens and xenon that emit in the blue, green and/or red, and HPLDs may be used.

NIR Imaging Module

The device 150 further includes an image acquisition functionality. In other embodiments, illumination and image acquisition may be handled by the same proximal modules.

Infra red image acquisition may be achieved using any sensor capable of detecting an infra red fluorescent signal that is positioned to detect infrared light energy from afocal assembly 11 and virtual pupil 13. In certain embodiments a plurality of sensors are provided. Examples include silicon based sensors, composite metal oxide semi oxide (CMOS) sensors and photographic film. In one embodiment the sensor comprises a camera, e.g. charge coupled device (CCD). Examples of a CCD include the Hitachi KP-M2; KP-M3 (Hitachi, Tokyo, Japan). In some embodiments, the sensor comprises a video camera. In certain embodiments the sensor may capture images at the rate of at least 10 per second, at least 15 per second, at least 20 per second, at least 30 per second, or at least 50 per second. Thus, in certain embodiments the invention contemplates a plurality of images. In other embodiments the invention contemplates at least one image.

The camera may be comprised of a means for focusing the image. In certain embodiments the invention contemplates a manual means for focusing an image. In other embodiments the invention contemplates an automated means for focusing an image. The camera may further be comprised of a lens system that permits magnification of an image field.

In certain embodiments the camera relays the captured image to an analog to digital converter and then through image capture and processing software running on a computer that is in electrical communication with the detectors. The image capture and processing software relays an image to a monitor or viewing device through which the user can view the image. In another embodiment, the image is relayed to a monitor in electrical communication with the computer. The image may be stored in any suitable medium, e.g., a hard drive, an optical disk, magnetic tape. The camera may also direct images to a television/VCR system such that the images may be displayed in real time, recorded and played back at a later time.

Visible Light Imaging Module

As described above, the device 150 preferably images in both the infrared and visible spectrums. Thus, a dye that emits light in the visible spectrum may be administered to a subject. For example, the dye may be fluorescein, which has an absorption maximum at 490 nm and an emission maximum of 514 nm (in water). Thus, one or more imaging modules include a light source that to excite this visible dye and detectors to detect light energy emitted by the visible dye.

In some embodiments, device 150 includes or is configured to receive a visible light imaging module. It includes one or more detectors that are configured to receive visible light energy from afocal assembly 12 that is relayed through the virtual pupil 13. One or more of the detectors may be a polychromatic detector, such as a single CCD or CMOS detector with an integrated color filter, such as a Bayer pattern directly on the detector. In another embodiment, the one or more detectors include a set of detectors, with at least one configured to detect red, another configured to detect blue and yet another configured to detect green. The detectors transmit data to a computer having image processing software which processes the detected information and forms one or more images. The images can then be displayed on a monitor or ocular that is in electrical communication with the computer.

Focusing Detectors/Cameras

One or more of the detectors/cameras used to detect in the visible or infrared spectrums may be comprised of a means for focusing the image. In certain embodiments the invention contemplates a manual means for focusing an image. In other embodiments the invention contemplates an automated means for focusing an image. The camera may further be comprised of a lens system that permits magnification of an image field.

Treatment Module

The skilled artisan is familiar with treatment methods including light energy, e.g., photocoagulation. For example, U.S. Pat. Nos. 5,394,199 and 6,351,663 disclose photocoagulation methods. They are both herein incorporated by reference in their entirety.

The treatment module relays light energy of sufficient wavelength and intensity for such therapy through the virtual pupil 13 and to afocal assembly 11. Afocal assembly 12 transmits it to the subject's eye.

The skilled artisan will understand that treatment radiation in the infrared will be focused on the subject choroidal neovasculature 1 while treatment radiation in the visible spectrum will be aimed at the retina 2. Thus, the treatment module includes or is optically in communication with a light source that emits radiation in one or both visible or infra red wavelengths.

METHODS OF THE INVENTION

In certain embodiments the invention provides a method for imaging at least one vessel comprising a part of the vasculature in a subject. The image may be obtained non-invasively. The method comprises administering at least one fluorescent dye to the subject, applying a form of radiant energy to the vessel such that the fluorescent dye fluoresces and obtaining an image of the vessel.

In other embodiments, the method includes the steps of imaging in the visible spectrum. Such imaging can be achieved by administered a dye that emits energy in the visible spectrum, exciting the dye, and detecting its emission.

In certain embodiments the vessel may be associated with the eye, e.g. the choroid, the retina. The vessel may be part of a vasculature abnormality, e.g. diabetic retinopathy, choroidal neovascularization (CNV). The method may also comprise treating a vessel that is part of a vasculature abnormality. Treatment may comprise photocoagulating the vessel or photocoagulating a feeder vessel. A feeder vessel may be a vessel that transports blood to another vessel.

The invention also contemplates obtaining a plurality of images. The plurality of images may be taken simultaneously. The images may be superimposed or fused with one another. The plurality of images may be compared to each other to determine the effectiveness of a therapy, e.g. an administered pharmaceutical compound, a surgical procedure.

Dyes

Suitable fluorescent dyes include any non-toxic dye which fluoresces when exposed to radiant energy, e.g. light. In certain embodiments the dye is a fluorescent dye that emits light in the infra red spectrum. In certain embodiments the dye is tricarbocyanine dye such as indocyanine green (ICG). In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The aforementioned dyes may be mixed or combined in certain embodiments. In some embodiments dye analogs may be used. A dye analog includes a dye that has been chemically modified, but still retains its ability to fluoresce when exposed to radiant energy of an appropriate wavelength.

A number of dyes that emit in the visible spectrum are known to the skilled artisan. For example, fluorescein isothiocyanate fluorescein or sodium fluorescein are commonly used for imaging the eye.

In some embodiments only one dye may be administered to the subject. In another embodiment, multiple dyes are administered. Preferably, both a dye that emits light in the infra red spectrum and a dye that emits in the visible light spectrum are administered. The two dyes may be administered simultaneously or sequentially.

The dye(s) may be administered intravenously, e.g., as a bolus injection. In other embodiments, the dye(s) may be administered directly into the eye with a dropper. In some embodiments the administered dye may comprise a volume of about 0.5 ml. In other embodiments it may include a volume in the range of about 0.1 ml to about 10 ml. In some embodiments the dye may be administered parenterally.

The dye(s) may be administered at a suitable concentration such that the fluorescence may be detected when the appropriate wavelength of radiant energy is applied. In some embodiments where the dye is ICG a suitable concentration is about 0.03 mg/ml at the site of detection. In other embodiments a suitable concentration of ICG is in the range of about 0.003 mg/ml to about 75 mg/ml. In yet other embodiments the dye is administered at a concentration of about 0.5 mg/kg body weight. In still other embodiments the dye is administered in a range of about 0.01 mg/kg body weight to about 3 mg/kg body weight.

The dye may be provided as a lyophilized powder or solid. In certain embodiments it may be provided in a vial, e.g., a sterile vial which may permit reconstitution with a sterile syringe. It may be reconstituted using any appropriate carrier or diluent. Examples of carriers and diluents are provided below. In certain embodiments the dye may be reconstituted at a concentration in the range of about 1 mg/ml-100 mg/ml. In other embodiments the dye is reconstituted to a concentration of about 10 mg/ml, about 20 mg/ml, about 30 mg/ml, about 40 mg/ml, about 50 mg/ml. The dye may be reconstituted, e.g., with water, immediately before administration.

In certain embodiments the dye may be administered to the subject less than an hour in advance of obtaining an image. In some embodiments the dye may be administered to the subject less than 30 minutes in advance of obtaining an image. In yet other embodiments the dye may be administered at least 30 seconds in advance of obtaining an image. In still other embodiments the dye is administered contemporaneously with obtaining an image.

Diluents and Carriers

Any diluent or carrier which will maintain the dye in solution may be used. As an example, in certain embodiments where the dye is ICG the dye may be reconstituted with water. In other embodiments where the dye is ICG, the dye may be reconstituted with an alcohol, e.g. ethyl alcohol. In some embodiments once the dye is reconstituted it may be mixed with additional diluents and carriers. In some embodiments the dye may conjugated to another molecule, e.g., a protein, a peptide, an amino acid, a synthetic polymer, or a sugar, e.g., to enhance solubility or to enhance stability.

Additional examples of diluents and carriers which may be used in the invention include glycerin, polyethylene glycol, propylene glycol, polysorbate 80, Tweens, liposomes, amino acids, lecithin, dodecyl sulfate, phospholipids, deoxycholate, soybean oil, vegetable oil, safflower oil, sesame oil, peanut oil, cottonseed oil, sorbitol, acacia, aluminum monostearate, polyoxylethylated fatty acids, and mixtures thereof. Additional buffering agents may optionally be added including Tris, HCL, NaOH, phosphate buffer, HEPES.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A device for visualizing one or more of the choroids and retina in the eye of a subject comprising:
    (a) an afocal assembly comprising an objective assembly and a collimating assembly, wherein the objective assembly is configured to relay an aerial image of the subject's eye to the collimating assembly, and the collimating assembly collimates the image and relays it to an external pupil in image space;
    (b) one or more proximal modules that are in optical communication with the afocal assembly through the external pupil; and
    a proximal radiation module that emits radiation of sufficient wavelength and intensity to photocoagulate a dye.

2. The device of claim 1, wherein the diameter of the ray bundle entering the afocal assembly from the one or more proximal modules is larger than the diameter of the ray bundle that is transmitted to the subject's eye.

3. The device of claim 2, wherein the device comprises telecentric image space.

4. The device of claim 1, wherein the external pupil comprises a first zone and a second zone, wherein the first zone is allocated for light energy traveling from one or more proximal modules to the afocal assembly, and the second zone is allocated for light energy traveling from the afocal assembly to one or more proximal modules.

5. The device of claim 1, wherein the device comprises a first proximal module that emits light energy in the infrared spectrum, said light energy being directed from the first proximal module to the afocal assembly through the external pupil.

6. The device of claim 1, wherein the device comprises a second proximal module that emits light energy in the visible spectrum, said light energy being directed from the first proximal module to the afocal assembly through the external pupil.

7. The device of claim 1, wherein the device comprises a third proximal module that comprises detectors for detecting light energy from the afocal assembly.

8. The device of claim 1, wherein the device comprises a fourth proximal module that emits a fixation beam.

9. The device of claim 1, further comprising one or more telecentric lenses distal to one or more of the distal assemblies and proximal to the exterior pupil.

10. The device of claim 1, wherein the one or more proximal assemblies have an external proximal device pupil.

11. A method of visualizing a subject's eye, comprising:
    (a) administering to the subject at least one of a first dye and a second dye that emits in the infra red spectrum when it is excited; and
    (b) imaging the subject's choroidal neovasculature or photocoagulating the second dye with the device of claim 1.

12. The method of claim 11, further comprising administering to the subject a third dye that emits in the visible spectrum when it is excited and imaging the subject's retina with the device of claim 1.

13. The method of claim 12, wherein the first dye is indocyanine green and the third dye is sodium fluorescein.

* * * * *